US012642965B2

(12) United States Patent
Tellenbach

(10) Patent No.: US 12,642,965 B2
(45) Date of Patent: Jun. 2, 2026

(54) NEUROMUSCULAR ELECTRICAL STIMULATION DEVICE WITH AUTOMATED SWITCHABLE REGULATION TECHNOLOGIES

(71) Applicant: NMES Group AB, Svenljunga (SE)

(72) Inventor: Vincent Tellenbach, Sion Valais (CH)

(73) Assignee: NMES Group AB, Svenljunga (SE)

( * ) Notice: Subject to any disclaimer, the term of this patent is extended or adjusted under 35 U.S.C. 154(b) by 322 days.

(21) Appl. No.: 18/030,960

(22) PCT Filed: Oct. 11, 2021

(86) PCT No.: PCT/EP2021/078020
§ 371 (c)(1),
(2) Date: Apr. 7, 2023

(87) PCT Pub. No.: WO2022/074254

PCT Pub. Date: Apr. 14, 2022

(65) Prior Publication Data

US 2023/0381513 A1    Nov. 30, 2023

Related U.S. Application Data

(60) Provisional application No. 63/198,321, filed on Oct. 10, 2020.

(51) Int. Cl.
*A61N 1/36* (2006.01)
*A61N 1/04* (2006.01)
(52) U.S. Cl.
CPC ........ *A61N 1/36034* (2017.08); *A61N 1/0452* (2013.01); *A61N 1/0456* (2013.01)

(58) Field of Classification Search
CPC . A61N 1/36034; A61N 1/0452; A61N 1/0456
(Continued)

(56) References Cited

U.S. PATENT DOCUMENTS

2007/0191907 A1    8/2007    Stein et al.
2010/0114252 A1    5/2010    Torgerson
(Continued)

FOREIGN PATENT DOCUMENTS

CN        205434688 U    8/2016
WO    WO 2015/042682 A1    4/2015

OTHER PUBLICATIONS

International Search Report dated Feb. 2, 2022, for International Application No. PCT/EP2021/078020.

*Primary Examiner* — Nadia A Mahmood
(74) *Attorney, Agent, or Firm* — Wolf, Greenfield & Sacks, P.C.

(57)    ABSTRACT

A device for providing electrical stimulation to muscles and nerves using two distinct regulation technologies with automatic switching capability for the treatment of medical and non-medical conditions. NeuroMuscular Electrical Stimulation (NMES) and Transcutaneous Electrical Nerve Stimulation (TENS) consists of delivering short electrical impulses to the user. These impulses can be regulated either in voltage or in electrical current. This device features both regulation technologies and has the capability to select the most efficient regulation technology based on the response of the stimulated object (individual) to the electrical impulses.

20 Claims, 8 Drawing Sheets

(58) Field of Classification Search
USPC .......................................................... 607/59
See application file for complete search history.

(56) References Cited

U.S. PATENT DOCUMENTS

| | | | |
|---|---|---|---|
| 2010/0114257 A1* | 5/2010 | Torgerson | G01R 31/3647 |
| | | | 607/63 |
| 2011/0112605 A1 | 5/2011 | Fahey | |
| 2014/0343625 A1 | 11/2014 | O Laighin et al. | |
| 2017/0197077 A1 | 7/2017 | Harpak et al. | |
| 2020/0147389 A1 | 5/2020 | Boor et al. | |

* cited by examiner $$I = V / R$$

NEUROMUSCULAR ELECTRICAL STIMULATION DEVICE WITH AUTOMATED SWITCHABLE REGULATION TECHNOLOGIES

CROSS REFERENCE TO RELATED APPLICATIONS

This Application is a national stage filing under 35 U.S.C. § 371 of International Patent Application Serial No. PCT/EP2021/078020, filed on Oct. 11, 2021, entitled NEUROMUSCULAR ELECTRICAL STIMULATION DEVICE WITH AUTOMATED SWITCHABLE REGULATION TECHNOLOGIES, which claims the benefit of U.S. Provisional Application No. 63/198,321, filed on Oct. 10, 2020. The contents of these applications are incorporated herein by reference in their entirety.

FIELD OF THE INVENTION

The present invention relates, in general, to the use of electrical stimulation of muscles and nerves for the purpose of alleviating a broad range of medical conditions as well as for specific non-medical objectives.

BACKGROUND

The number of medical applications that use electrical stimulation is large and covers virtually every living body component. These applications include prevention of muscle atrophy, promotion of wound healing, prevention of venous thrombosis, alleviation of both chronic/acute pain and prevention of incontinence to name but a few. Electrical stimulation may also be used for such non-medical objectives as muscle training, muscle toning, improving muscle endurance, and muscle relaxation.

Electrical stimulation of muscles and nerves is well established in medicine and physical therapy with a history dating back to mid-1850; such stimulation is currently achieved by applying electrodes to: 1) the skin at the point(s) of desired electrical stimulation; 2) through insertion of electrical probes into body cavities, and; 3) through surgical insertion of electrodes.

Neuromuscular Electrical Stimulation Principle

Muscle contractions are produced and controlled by the brain by means of electrical signals transmitted through the nervous system. When an electrical signal from the brain reaches the muscle, the latter is activated into groups of "motor units", each made up of a single neuron and of a group of associated muscle cells connected to it. This initiates a chemical reaction which causes the cells in this motor unit to contract. The complete contraction of the muscle usually involves a number of motor units simultaneously, and its strength is directly proportional to the number of activated motor units. The gradual enrolment process of the motor units which consents to a perfectly controlled and smooth muscle contraction is called spatial summation.

Electrical muscle stimulation (EMS), also known as neuromuscular electrical stimulation (NMES) or electromyostimulation, is the elicitation of muscle contraction using electric impulses. The impulses are generated by a device and are delivered through electrodes on the skin near to the muscles being stimulated. The electrodes are generally pads that adhere to the skin. The impulses mimic the action potential that comes from the central nervous system, causing the muscles to contract.

When a sufficiently intense single electrical impulse reaches the motor muscle or nerve, it causes one short single contraction of the muscle (spasm). If this single spasm is repeated and the frequency of reiteration exceeds ten spasms p.s., each following spasm is enhanced by one degree of muscle shortening caused by the preceding spasm. Such an effect is called temporal summation. The lowest stimulation frequency, where the successive contractions merge, is called tetanization frequency.

Thus, electrical stimulation of muscles and nerves consists in the delivery of short electrical impulses. These impulses can be controlled (or regulated) by voltage regulation or by electrical current regulation. Both technologies have their own advantages and disadvantages. Electrical current regulation is better suited for precise electrical stimulation requiring small electrodes while voltage regulation is better suited for larger electrodes or electrodes that slightly move on the skin.

Existing portable Neuromuscular Electrical Stimulation (NMES) devices and Transcutaneous Electrical Nerve Stimulation (TENS) devices propose one of the two regulation technologies.

Some more complex or clinical units using both technologies will rely on the expert medical knowledge to select which technology is better suited for a specific treatment. Only an experienced person can assess the differences between the two technologies, and thus, to date, such units are limited to clinical settings and by the presence of a trained professional.

SUMMARY

The invention is defined by the appended independent claims. Embodiments of the invention are defined in the dependent claims.

In a first aspect of the invention, there is provided a device for providing an electrical stimulation impulse to a user, comprising: a conductive medium configured to apply the electrical stimulation impulse to a user; a voltage regulator, configured to regulate the voltage applied during the electrical stimulation impulse; a current regulator, configured to regulate the current applied during the electrical stimulation impulse; and a selector module, configured to: determine which of voltage regulation and current regulation will deliver more charge during the electrical stimulation impulse; and output a result of the determination.

In this way, the device according to the present invention can provide an informed and valuable output determination, informing whether voltage regulation or current regulation will be more efficient, i.e. which will deliver the greater charge to the user of the device. By providing a more efficient device, the power consumption of the device can be reduced. This may be advantageous to reduce the heat and noise generated by the device. Furthermore, if the device incorporates a portable power supply, for example a battery, the power supply may be made smaller while maintaining similar device run time and/or the run time may be increased for a certain size of power supply.

Additionally, the ability of the device to determine which of voltage and current regulation will be more effective, without the need for an experienced practitioner, allows the device to be suitable for use outside a medical setting. This not only allows users more freedom as to when they use the device, but also where they use the device, allowing the device to be portable yet still effective, efficient, and safe to use.

The conductive medium may comprise: a conductive garment; a conductive accessory; or one or more hydrogel electrodes. In this way, the conductive medium may be able to apply charge where it is desired and/or effective for a user.

The selection module may comprise a processor configured to perform the determination and outputting steps, as well as further steps to be described relating to the selection module. Alternatively, the selector module may be configured to communicate with a remote processor, for example comprised within a mobile device communicatively linked with the stimulation device via a wireless communications protocol such as Bluetooth (e.g. Bluetooth Low Energy), and/or with a separate local processor communicatively coupled with the stimulation device via a wired connection. In each case, a person skilled in the art will appreciate the hardware components required for transmission and reception of data with a remote processing unit and for wired communication with a local processing unit.

The selector module may be further configured to: select and activate either the voltage regulator or the current regulator, selecting and activating whichever is determined will deliver more charge during the electrical stimulation impulse.

In this way, the device can automatically select one of voltage and current regulation and prepare the device for the delivery of the electrical stimulation impulse. This mode of operation may be useful for end-users, i.e., those to whom the impulse is being delivered, who may not have the expertise necessary to make the voltage versus current determination themselves. The device is therefore able to provide effective, efficient, and safe electrical stimulation impulses.

Furthermore, by removing the need for a user to select one of the regulation modes, elements of the user interface of the device may be simplified or removed entirely. This may reduce the size and/or complexity of the device. It is advantageous for devices suitable for providing electrical stimulation to muscles and/or nerves to be as small as possible. Some forms of such devices may need to be worn during exercise, such that both weight and physical size are important parameters, and even those worn while the user is stationary may be advantageously reduced in size to aid portability and ease of use. Reducing the number of electrical components in the device reduces both the weight and size of the device.

The device may further comprise: a display, configured to display the result of the determination; and a user interface, configured to receive a selection of voltage or current regulation from a user, and wherein the selector module is further configured to: activate either the voltage regulator or the current regulator, activating whichever is selected by the user via the user interface.

In this way, the device can operate in a 'recommendation' mode, wherein the output of the determination is displayed to the user, but the activation of the recommended regulator is not automatic. This provides flexibility in the operating characteristics of the device, because a user with expertise and/or knowledge of a parameter not available to the device can override the recommendation in some circumstances.

The display may, alternatively or additionally, be a means for audio feedback, for example a speaker, an alternative visual cue, for example a pair of light emitting diodes (LEDs), or any other means by which a user may be informed of the result of the determination.

The conductive medium may comprise at least two terminals, and, when determining which of voltage and current regulation will deliver more charge during the electrical stimulation impulse, the selector module may be further configured to: calculate a resistance between the terminals; and make the determination based on the calculated resistance.

This has been found to be a particularly effective way for the device to determine which of voltage and current regulation will be most effective and efficient, i.e., deliver the maximum charge.

Terminals, as used herein, refer to electrically conductive points connected to the stimulation device. In use, the terminals may be separated by the skin of user, thus it is the resistance of the skin of a user that is calculated when calculating the resistance between the terminals. The terminals may, for example, be two distinct electrodes on a single patch of a conductive medium, or, in an alternative example, be a first electrode on a first patch and a second electrode on a second patch.

The selector module may be further configured, when calculating a resistance between the terminals, to: select voltage regulation; deliver a test voltage through the terminals of the conductive medium for a time period; measure the electrical charge delivered through the terminals of the conductive medium during the time period; and calculate the resistance between the terminals based at least on the measured electrical charge and the time period.

In this way, the device can effectively and reliably calculate the resistance between the terminals, providing accurate information with which to make the determination between voltage and current regulation.

The test voltage may be selected by the selection module to be sufficiently low so as not to be perceived by a user when delivered through the terminals of the conductive medium. In this way, the user may not experience any discomfort and/or unexpected stimulation during the determination stage. Furthermore, power consumption during the determination stage is limited by the use of low voltage.

The selector module may be further configured to: calculate a resistance value, $R_{mid}$, for which voltage regulation and current regulation would deliver equal charge; compare $R_{mid}$ to the resistance calculated between the terminals; and determine that voltage regulation will deliver more charge during the electrical stimulation impulse if the resistance calculated between the terminals is lower than $R_{mid}$, and determine that current regulation will deliver more charge during the electrical stimulation impulse if the resistance calculated between the terminals is greater than $R_{mid}$.

This has been found to be a particularly effective way for the device to determine which of voltage and current regulation will be most effective and efficient, i.e., deliver the maximum charge.

The device may further comprise a current integrator configured to measure the electrical charge delivered through the terminals of the conductive medium during the time period. The use of a current integrator is one way in which the charge delivered may be measured, however, any suitable method to measure charge may be used as will be appreciated by a person skilled in the art.

The voltage regulator and the current regulator may share at least one electrical component with one another. Optionally, the at least one shared electrical component comprises an H-bridge and/or a boost converter. Optionally, when the voltage regulator is active, the boost converter provides a voltage set by the device, and the voltage regulator drives switches of the H-bridge to deliver maximum electric current. Optionally, when the current regulator is active, the boost converter provides a maximum voltage, the current regulator drives switches of the H-bridge to maintain a constant electrical current.

In this way, the number of necessary electrical components in the device is advantageously reduced. The physical size of the device, and its power consumption, can be reduced. Since there is no state in which both voltage and current regulation are employed simultaneously, no functionality is sacrificed. The advantages of reductions in size and power consumption for devices such as that of the present invention are detailed above.

The selection module may comprise a plurality of switches configured selectively to connect the voltage regulator and the current regulator to the conductive medium.

After activating either the voltage regulator or the current regulator, the device may be configured to: deliver the electrical stimulation impulse. In this way, all of the advantages relating to the correct determination and activation of voltage or current regulation are realised during an actual electrical stimulation impulse.

After delivering the electrical stimulation impulse, the device may be further configured to: repeat the determination, output, selection, and activation of either voltage regulation or current regulation.

In this way, the most efficient regulation technology can be used at all times, including in cases where this changes either during stimulation patterns and/or between subsequent patterns. The resistance felt by the conductive medium, for example the resistance between the terminals, may change during stimulation, due to any number of factors, but including the effects of the stimulation itself. By re-determining the most appropriate regulation technology, maximum efficiency is achieved. It will be appreciated that the delivery of a stimulation impulse and the determination of the most efficient regulator technology may occur any number of times, and in any order; as may be necessary based on changes in the resistance between the terminals.

It will be appreciated that electrical stimulation impulses are often delivered in patterns and/or programs of impulses. A pattern and/or program may, for example, consist of impulses ramping upwards in amplitude and then consistent amplitude pulses for differing time durations. The further electrical stimulation impulse as claimed may be part of the same pattern and/or program of impulses, or a different patent and/or program of impulses. In other words, the determination as to whether voltage regulation or current regulation is more efficient may be made before a pattern of electrical stimulation impulses, during an ongoing pattern of electrical stimulation impulses, or between a plurality of patterns of electrical stimulation impulses. At each stage, the determination may either instruct a user as described herein or affect a change in regulation technology as also described herein.

In a second aspect of the invention, there is provided a method for providing an electrical stimulation impulse to a user, comprising: providing a conductive medium configured to apply the electrical stimulation impulse to a user; providing a voltage regulator, configured to regulate the voltage applied during the electrical stimulation impulse; providing a current regulator, configured to regulate the current applied during the electrical stimulation impulse; and determining, at a selector module, which of voltage regulation and current regulation will deliver more charge during the stimulation impulse; and outputting a result of the determination.

The method may further comprise: selecting and activating either the voltage regulator or the current regulator, selecting whichever is determined will deliver more charge.

The method may further comprise: displaying the result of the determination on a user interface; and receiving a selection of voltage or current regulation from a user via the user interface.

The conductive medium may comprise at least two terminals, and wherein, determining which of voltage and current regulation will deliver more charge during the electrical stimulation impulse comprises: calculating a resistance between the terminals; and making the determination based on the calculated resistance.

Calculating a resistance between the terminals may comprise: selecting voltage regulation; delivering a test voltage through the terminals of the conductive medium for a time period; measuring the electrical charge delivered through the terminals of the conductive medium during the time period; and calculating the resistance between the terminals based at least on the measured electrical charge and the time period.

The method may further comprise: calculating a resistance value, $R_{mid}$, for which voltage regulation and current regulation would deliver equal charge; comparing $R_{mid}$ to the resistance calculated between the terminals; and determining that voltage regulation will deliver more charge during the electrical stimulation impulse if the resistance calculated between the terminals is lower than $R_{mid}$, and determining that current regulation will deliver more charge during the electrical stimulation impulse if the resistance calculated between the terminals is greater than $R_{mid}$.

The method may further comprise: after activating either the voltage regulator or the current regulator, delivering the electrical stimulation impulse; repeating the determination, output, selection, and activation of either the voltage regulation or the current regulation; and delivering a further electrical stimulation impulse.

Advantages associated with the second aspect of the invention are the same as the respective advantages associated with the first aspect of the invention.

Methods according to the invention, as described herein, may be computer-implemented methods and may be used, where appropriate, for the delivery of electrical stimulation impulses for non-medical, or non-clinical, purposes, for example muscle conditioning.

The device described in the present invention enables the delivery of electrical stimulation using either voltage-controlled regulation or current-controlled regulation.

The device described in the present invention enables the automated selection of the most efficient regulation technology based on the physiological response of the stimulated object (individual).

The present invention may be used to treat or improve any muscular or neural condition that is alleviated through use of electrical stimulation.

The foregoing and other objects and advantages will appear from the descriptions that follow. In the description reference is made to the accompanying drawings, which forms a part hereof, and in which is shown by way of illustration specific principles of the control method in which the invention may be practiced. These principles will be described in sufficient detail to enable those skilled in the art to practice the invention, and it is to be understood that other principles may be utilized and that structural changes may be made without departing from the scope of the invention, for example, modifications in algorithms.

It is an object of the present invention to provide a device for electric stimulation that uses two different regulation technologies to provide for safe and effective transmission of electrical stimulation from the simulation device to the stimulation delivery medium, whether a conductive garment or a conductive accessory. It is an object of the present invention to provide a method for the automated selection of the most efficient regulation technology based on the response of the stimulated object (individual) to the electrical impulses. It is an object of the present invention to provide a device allowing the real time switching from one regulation technology to the other based on the response of the stimulated object (individual) to the electrical impulses. It is an object of the present invention to provide an alternative to the current practice of using only one regulation technology commonly used in handheld NMES and TENS devices. It is an object of the present invention to provide an alternative to the current practice of letting the user select the regulation technology in high end clinical NMES and TENS devices. An object of the present invention is to provide electric stimulation delivery that overcomes shortcomings in prior art devices. An object of the present invention is to provide an electric stimulation device, using two different automated switching regulation technologies, that delivers electrical impulses that trigger strong, effective muscle contractions or nerve responses in a stimulated object (individual). Another object of the present invention is to provide an electric stimulation device that may be safely operated by medical and non-medical users. A further object of the present invention is to provide electric stimulation that is simple and safe to use. A still further object of the present invention is to provide electric stimulation that is cost and size effective for both professionals and users.

DETAILED DESCRIPTION

Figure 1:
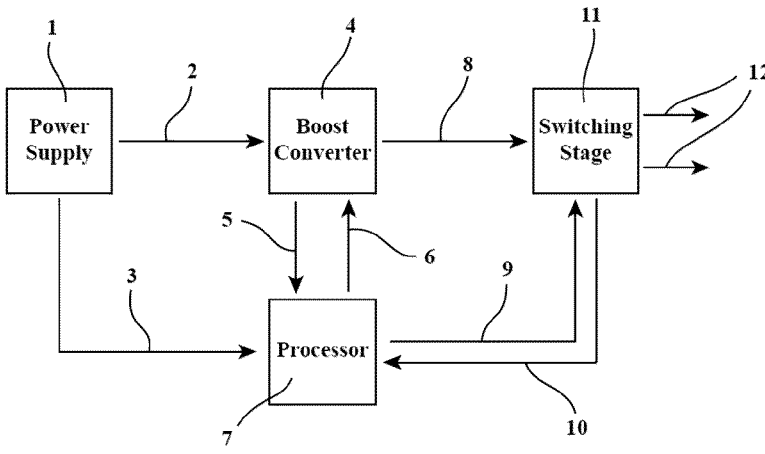
FIG. 1 shows a block diagram of the stimulation device.

FIG. 1 shows the block diagram of the stimulation device where (1) is the power supply element that provides electrical energy to the whole device (2)(3), (4) is the DC-DC boost converter element that boost the voltage provided by the power supply (1) up to the desired level (8), (5) is the feedback of the voltage of the DC-DC booster converter element provided to the processor (7), (6) is the DC-DC boost converter duty cycle that will be optimized accordingly to the determined electrical charge, (9) is the control of the switching stage (11) that will select the regulation technology and generates the electrical impulses delivered to the simulated object (individual) (12) and (10) is the feedback from the switching stage provided to the processor in order to determine the most efficient regulation technology to be used.

Figure 2:
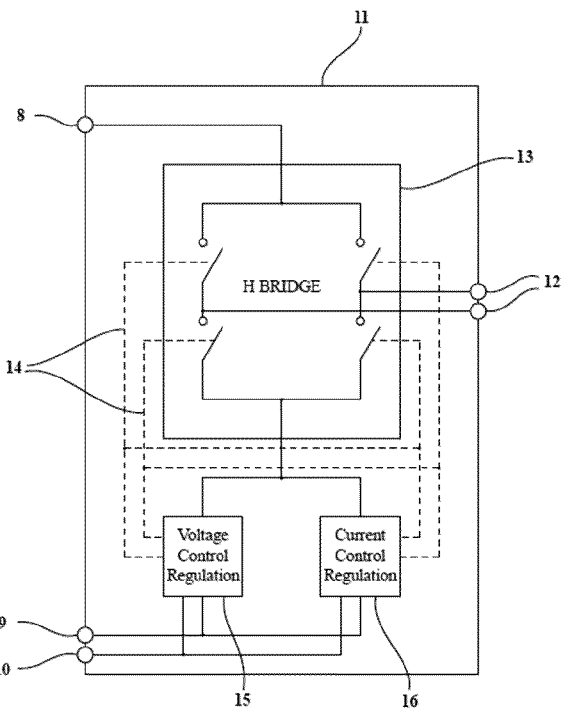
FIG. 2 shows a more detailed view of an embodiment of the stimulation device.

FIG. 2 shows a more detailed view of an embodiment of the switching stage (11). The voltage provided by the DC-DC boost converter (8) is applied to a H-bridge (13) that will deliver the electrical impulses to the simulated object (individual) (12). The switches of the H-bridge are driven by either the voltage control regulation module (15) or the electrical current control regulation module (16). The active regulation technology is selected by the processor (9) based on the feedback provided by the regulation modules (10). Further detail is provided below.

Human Body Impedance Model

Figure 3:
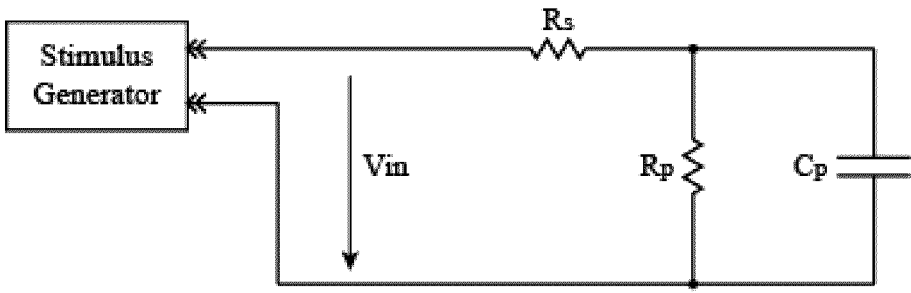
FIG. 3 shows equivalent electrical impedance of the human body.

According to the standard NS4:1986/(R)2009 from the Association for the Advancement of Medical Instrumentation (AAMI), the electrical impedance of the electrodes-skin system can be represented by the equivalent electrical circuit shown in FIG. 3, which shows equivalent electrical impedance of the human body.

Resistor $R_s$ represents the electrical resistance of the stimulus delivery system comprising the lead wires and electrodes. Resistor $R_p$ and capacitor $C_p$ represent an approximation of the impedance of the human body for a typical stimulus generator.

Kirchhoff's current law states that the algebraic sum of currents in a network of conductors meeting at a point is zero. Therefore, the electrical current flowing through resistor $R_s$ equals the sum of the electrical current flowing through resistor $R_p$ and capacitor $C_p$.

$$I_{Rs} = I_{Rp} + I_{Cp}$$

If capacitor $C_p$ is completely discharged at time=0, the following equations apply to FIG. 1:

At time=0

The electrical charge on capacitor $C_p$ being equal to zero at time=0, the voltage drop on $C_p$ and $R_p$ is equal to zero.

$$Q_{Cp_{t0}} = C_p \cdot V_{C_p} = 0 \rightarrow V_{C_p} = 0 \rightarrow V_{R_p} = 0$$

The electrical current flowing through resistor $R_s$ is:

$$I_{Rs_{t0}} = \frac{V_{in}}{R_s}$$

The current flowing through $R_p$ is zero because the voltage drop on $R_p$ is zero, therefor the current flowing through capacitor $C_p$ is equal to the current flowing through resistor $R_s$.

$$I_{Rp_{t0}} = 0, I_{Cp_{t0}} = I_{Rs_{t0}} = \frac{V_{in}}{R_s}$$

At time=∞

After a long period of time, the current flowing through capacitor $C_p$ is equal to zero. $C_p$ is considered as an open circuit. Therefor the electrical current flowing through to resistor $R_s$ is:

$$I_{Rs_{t\infty}} = \frac{V_{in}}{R_s + R_p}$$

The current flowing through resistor $R_p$ is the same as the current flowing through $R_s$:

$$I_{R_{p\infty}} = I_{R_{s\infty}} = \frac{V_{in}}{R_s + R_p} \rightarrow I_{C_{p\infty}} = 0$$

Transition

Between time=0 and time=∞, the voltage on capacitor $C_p$ increases and is equal to voltage on resistor $R_p$:

$$Q_{C_p} = C_p \cdot V_{C_p} \rightarrow V_{C_p} = \frac{Q_{C_p}}{C_p}$$

$$V_{R_p} = R_p \cdot I_{R_p} \rightarrow$$

$$V_{C_p} = V_{R_p} = R_p \cdot I_{R_p} = \frac{Q_{C_p}}{C_p}$$

The relation between the electrical current flowing through $R_s$, $R_p$ and $C_p$ is given by:

$$I_{Rs} = I_{Rp} + I_{Cp} \rightarrow$$

$$I_{Rs} = I_{Rp} + I_{Cp} = \frac{Q_{C_p}}{R_p \cdot C_p} + I_{Cp}$$

Input voltage Vin is equal to:

$$V_{in} = V_{R_s} + V_{R_p} = R_s \cdot \left( \frac{Q_{C_p}}{R_p \cdot C_p} + I_{Cp} \right) + \frac{Q_{C_p}}{C_p} \rightarrow$$

$$\frac{V_{in}}{R_s} = \frac{Q_{C_p}}{R_p \cdot C_p} + I_{Cp} + \frac{Q_{C_p}}{R_s \cdot C_p} \rightarrow$$

$$-I_{C_p} = \frac{Q_{C_p}}{R_p \cdot C_p} + \frac{Q_{C_p}}{R_s \cdot C_p} - \frac{V_{in}}{R_s}$$

Multiply both sides of the equation by $R_s \cdot C_p$:

$$-(R_s \cdot C_p) I_{C_p} = \frac{R_s \cdot Q_{C_p}}{R_p} + Q_{C_p} - C_p \cdot V_{in} \rightarrow$$

$$-(R_s \cdot C_p) I_{C_p} = \left( \frac{R_s}{R_p} + 1 \right) \cdot Q_{C_p} - C_p \cdot V_{in}$$

Replacing expression $$\frac{R_s}{R_p} + 1$$

with α to simplify the equation and replacing $I_{C_p}$ with the charge formula $dQ = I \cdot dt$ results in the following differential equation:

$$-(R_s \cdot C_p) \cdot \frac{dQ_{C_p}}{dt} = \alpha \cdot Q_{C_p} - C_p \cdot V_{in} = \alpha \cdot \left( Q_{C_p} - \frac{C_p \cdot V_{in}}{\alpha} \right)$$

Group the terms with $Q_{C_p}$ on one side of the equation:

$$\frac{dQ_{C_p}}{Q_{C_p} - \frac{C_p \cdot V_{in}}{\alpha}} = \frac{-\alpha}{R_s \cdot C_p} \cdot dt$$

Integrate the equation on both sides:

$$\int_0^{Q_{C_p}} \frac{dQ_{C_p}}{Q_{C_p} - \frac{C_p \cdot V_{in}}{\alpha}} = \int_0^t \frac{-\alpha}{R_s \cdot C_p} \cdot dt \rightarrow$$

$$\ln \left| \frac{Q_{C_p} - \frac{C_p \cdot V_{in}}{\alpha}}{-\frac{C_p \cdot V_{in}}{\alpha}} \right| = \frac{-\alpha}{R_s \cdot C_p} \cdot t$$

Get the exponential on both sides of the equation:

$$\rightarrow \frac{Q_{C_p} - \frac{C_p \cdot V_{in}}{\alpha}}{-\frac{C_p \cdot V_{in}}{\alpha}} = e^{\frac{-\alpha \cdot t}{R_s \cdot C_p}}$$

$$\rightarrow Q_{C_p}(t) = \frac{C_p \cdot V_{in}}{\alpha} \cdot \left( 1 - e^{\frac{-\alpha \cdot t}{R_s \cdot C_p}} \right)$$

The derivative of the expression on the right side with respect to time give the instantaneous value of the current flowing through capacitor $C_p$:

$$I_{C_p}(t) = \frac{V_{in}}{R_s} \cdot e^{\frac{-\alpha \cdot t}{R_s \cdot C_p}}$$

Using the formula $$R_p \cdot I_{R_p} = \frac{Q_{C_p}}{C_p},$$

the current flowing through resistor $R_p$ is:

$$I_{R_p}(t) = \frac{V_{in}}{\alpha \cdot R_p} \cdot \left( 1 - e^{\frac{-\alpha \cdot t}{R_s \cdot C_p}} \right)$$

Finally, the current flowing through resistor $R_s$ is given by:

$$I_{Rs}(t) = I_{Rp}(t) + I_{Cp}(t) = \frac{V_{in}}{R_s + R_p} \cdot \left( 1 - e^{\frac{-\alpha \cdot t}{R_s \cdot C_p}} \right) + \frac{V_{in}}{R_s} \cdot e^{\frac{-\alpha \cdot t}{R_s \cdot C_p}}$$

Current vs. Voltage Regulation For Electrical Stimulation

Electrical stimulation of muscles and nerves consists in the delivery of short electrical impulses. These impulses can be controlled (or regulated) in voltage or in electrical current. Both technologies have their own advantages and disadvantages. Electrical current regulation is better suited for precise electrical stimulation requiring small electrodes while voltage regulation is better suited for larger electrodes or electrodes that slightly move on the skin.

Figure 4:
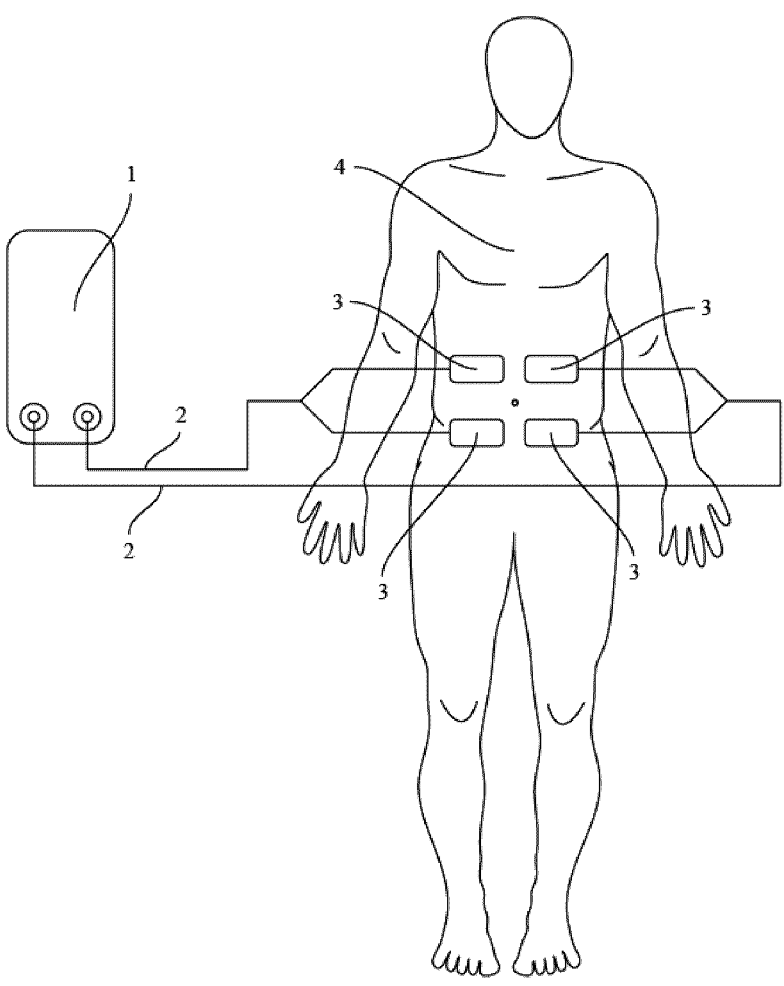
FIG. 4 shows a typical setup for neuromuscular electrical stimulation applications.

FIG. 4 represents a typical setup for neuromuscular electrical stimulation applications. A device (1) delivers the electrical stimulation treatment by means of lead wires (2) connected to a set of electrodes (3) to the stimulated object (4). For simplification purposes, the setup comprising the lead wires, electrodes and stimulated object is named stimulated system in the present document.

Figure 5:
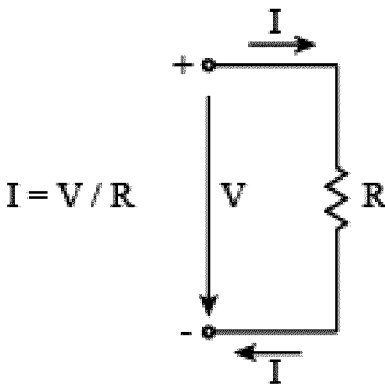
FIG. 5 shows Ohm's law with an electrical circuit.

The relation between the voltage and electrical current provided by the stimulation device (1) and the electrical impedance of the stimulated system is summarized by the law of Ohm formula: I=V/R where I is the current through the conductor in units of amperes, V is the voltage measured across the conductor in units of volts, and R is the resistance of the conductor in units of ohms. FIG. 5 illustrates Ohm's law with an electrical circuit.

The impedance of the stimulated system depends for the most part on the electrodes specification (i.e. size of the electrodes and quality of the conductive material), skin humidity and metabolism of the stimulated object. The larger the electrodes are, the lower the electrical impedance is.

Voltage Regulation

Figure 6:
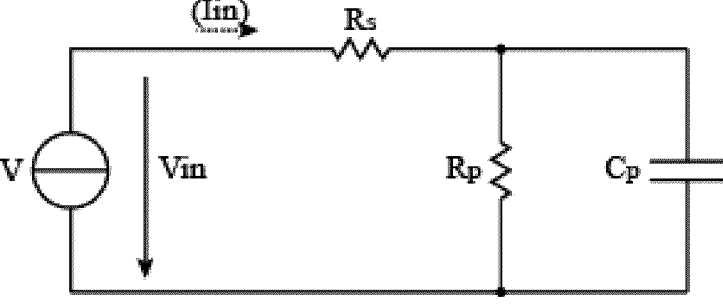
FIG. 6 shows a voltage regulation circuit model.

In a voltage regulated context, the setup presented in FIG. 4 can be modelized by the voltage regulation circuit of FIG. 6 where the stimulation device is represented by voltage generator V and the stimulated system are represented by the circuit of FIG. 3 comprising of resistors $R_s$, $R_p$ and capacitor $C_p$.

Figure 7:
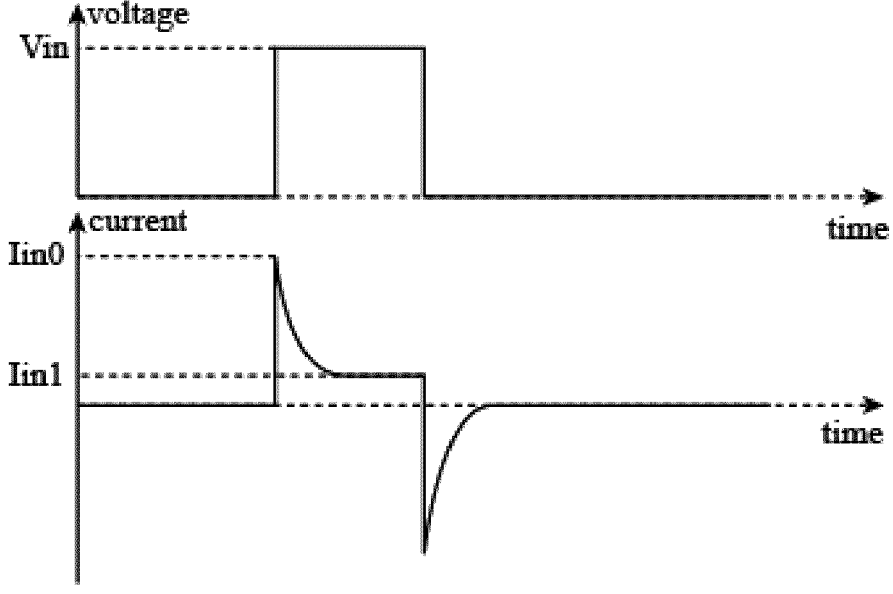
FIG. 7 shows a voltage regulation waveform.

The voltage Vin is fixed by voltage generator V. The resulting current $I_{in}$ is the response of the circuit to the application of voltage $V_{in}$. FIG. 7 shows the current resulting from a voltage regulated rectangular impulse (i.e. voltage regulation waveform). There is a spike of current $I_{in0}$ at the beginning of the impulse then, as capacitor $C_p$ reaches full charge, the current decreases until reaching a steady value $I_{in1}$ until the end of the impulse. As demonstrated in the previous paragraph:

$$I_{in0} = \frac{V_{in}}{R_s}; I_{in1} = \frac{V_{in}}{R_s + R_p}$$

Current Regulation

Figure 8:
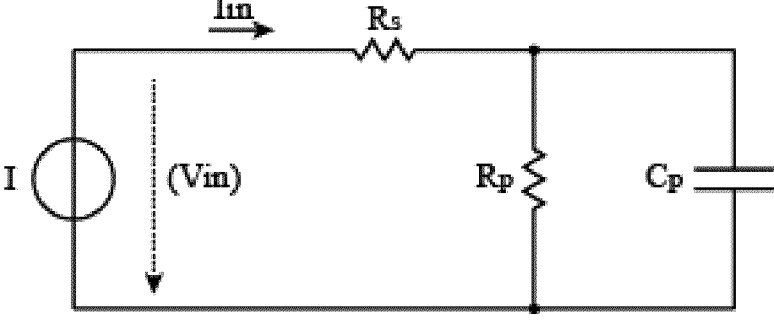
FIG. 8 shows a current regulation circuit model.

In a current regulated context, the setup presented in FIG. 4 can be modelized by the current regulation circuit of FIG. 8 where the stimulation device is represented by voltage generator I and the stimulated system are represented by the circuit of FIG. 1 comprising of resistors $R_s$, $R_p$ and capacitor $C_p$.

Figure 9:
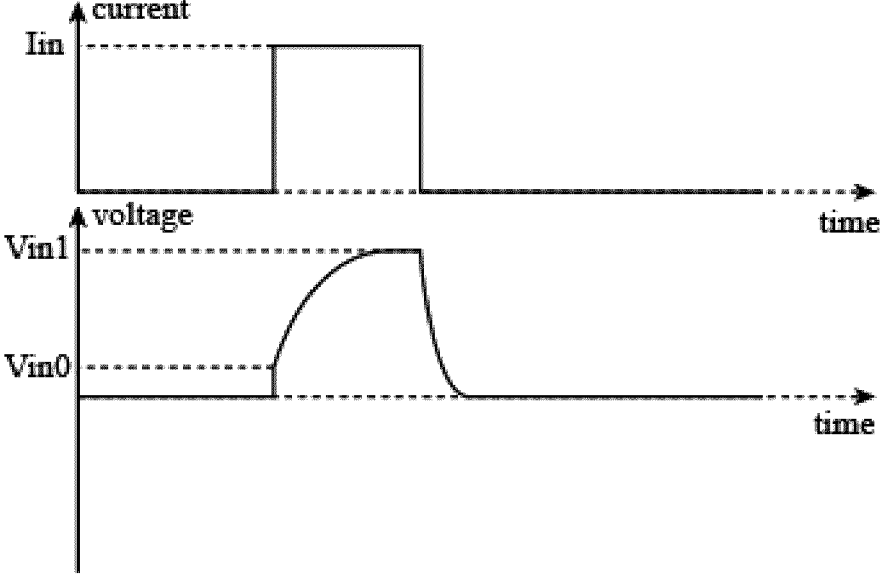
FIG. 9 shows a current regulation waveform.

The current $I_{in}$ is fixed by current generator I. The resulting voltage $V_{in}$ is the response of the circuit to the application of current $I_{in}$. FIG. 9 shows the voltage resulting from a current regulated rectangular impulse (i.e. a current regulation waveform). The voltage starts at $V_{in0}$ at the beginning of the impulse then, as capacitor $C_p$ reaches full charge, the voltage increases until reaching a steady value $V_{in1}$ until the end of the impulse. As demonstrated in the previous paragraph: $V_{in0}=I_{in}\cdot R_s$; $V_{in1}=I_{in}\cdot(R_s+R_p)$.

It is the object of the present invention to provide a device capable of delivering neuromuscular electrical stimulation with electrical impulses that can be either current regulated or voltage regulated. The maximal electrical current the device can deliver when using the current regulation is designated as $I_{MAX}$. The maximal voltage the device can deliver when using the voltage regulation is designated as $V_{MAX}$.

For a given impulse duration, the electrical charge delivered under a current regulation does not depend on the impedance of the stimulated system. It only depends on the electrical current and the impulse duration:

$$Q=I_{in}\cdot dt$$

Where Q is the electrical charge delivered to the stimulated system, $I_{in}$ is the electrical current set by the device and dt is the impulse duration.

At the opposite and for the same impulse duration, the electrical charge delivered under a voltage regulation will depend on the impedance of the stimulated system. Note: for simplification purposes the following formula only considers the electrical current steady value represented by $I_{in1}$ on FIG. 7. Therefore as only the resistive aspect of the stimulated system impedance is taken into account, the stimulated system impedance can also be designated as resistance.

$$Q = \frac{V_{in}}{R_s + R_p} \cdot dt$$

Where Q is the electrical charge delivered to the stimulated system, $V_{in}$ is the voltage set by the device and dt is the impulse duration.

Figure 10:
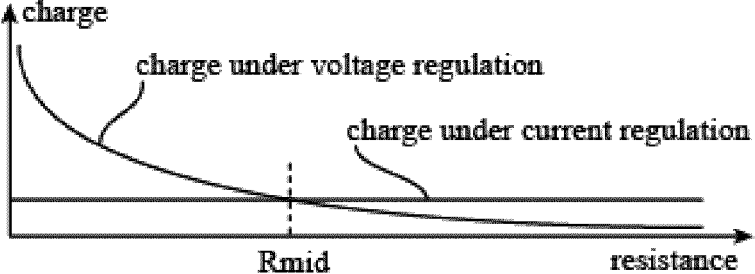
FIG. 10 shows a current versus voltage regulation charge comparison.

FIG. 10 shows the charge values for both current and voltage regulation technologies with respect to the resistance of the stimulated system (i.e. current vs. voltage regulation charge comparison).

Where $R_{mid}$ represents the stimulated system resistance value for which both regulation technologies have the same efficiency when set at their maximal specification. $R_{mid}$ can be assessed with the following formula:

$$R_{mid} = \frac{V_{MAX} \text{ when device is in voltage regulation}}{I_{MAX} \text{ when device is in current regulation}}$$

If the stimulated system resistance is lower than $R_{mid}$, using the voltage regulation will be more efficient and deliver a higher electrical charge. If the stimulated system resistance is greater than $R_{mid}$ then using the current regulation will be more efficient and deliver a higher electrical charge.

Assessment of the Stimulated System Resistance

In order to select the most efficient regulation technology it is necessary to assess the resistance of the stimulated system. To do so, the device must use the voltage regulation to apply a low voltage on the stimulated system for a given duration. This low voltage will not be perceived by stimulated object. The device must be able to measure the electrical charge delivered to the stimulated system. Either by having dedicated electronic components that can integrate the electrical current delivered to the stimulated system or by another method.

Procedure to Assess the Resistance of the Stimulated System
1. Select the voltage regulation
2. Deliver a low voltage to the stimulated system for a given duration
3. Measure the electrical charge delivered to the stimulated object
4. Determine the resistance using the formula $$Q = \frac{V_{in}}{R_s + R_p} \cdot dt \rightarrow R_s + R_p = \frac{V_{in}}{Q} \cdot dt$$

5. If $R_s+R_p<R_{mid}$ then voltage regulation will be better suited for the electrical stimulation treatment otherwise current regulation will be more efficient.

Figure 11:
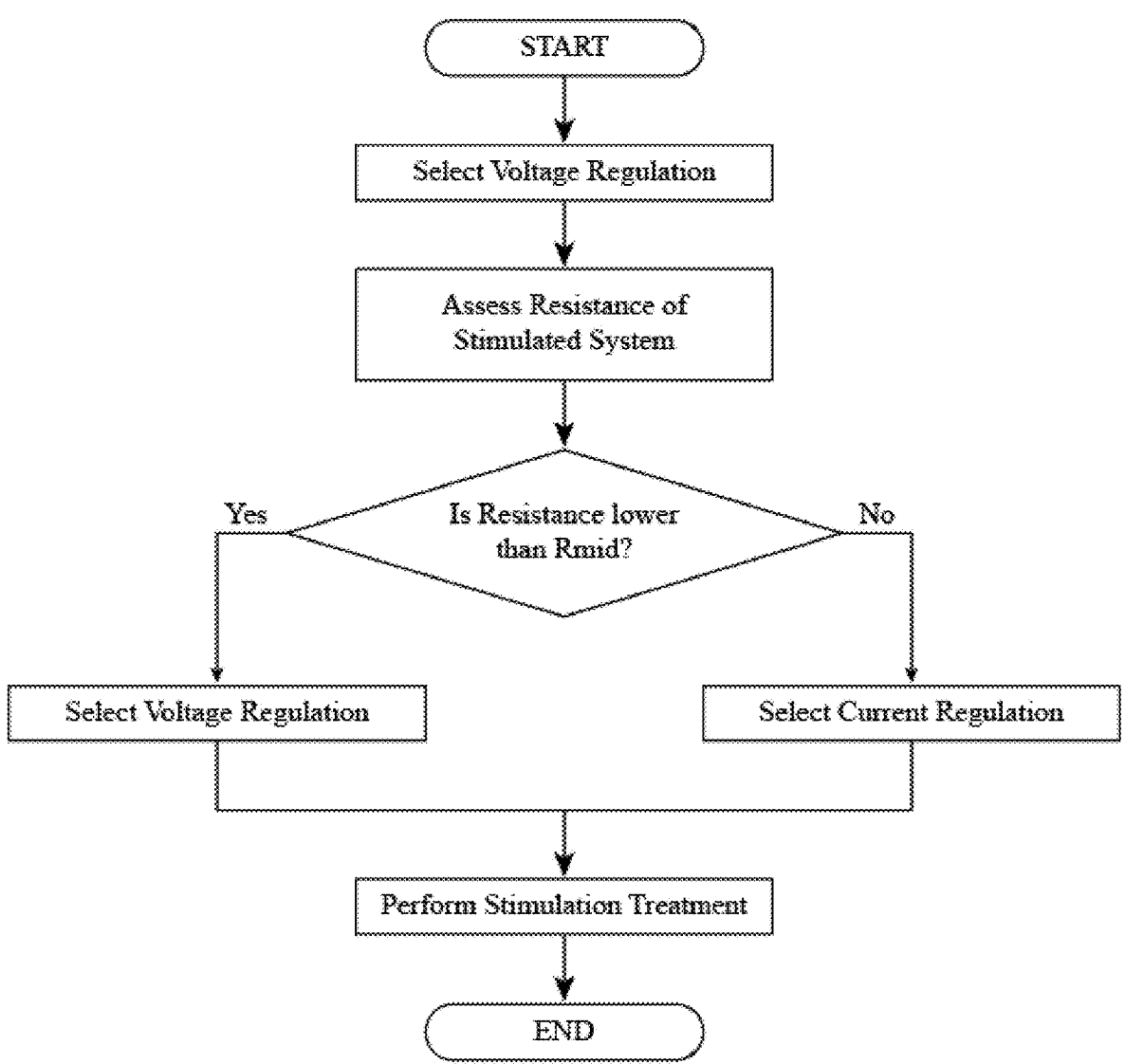
FIG. 11 shows a process for the assessment of resistance procedure.

FIG. 11 represents a process for the assessment of resistance procedure.

This procedure can be repeated during the stimulation treatment to re-assess the resistance of the stimulated system which can vary during the treatment.

The NMES device will offer two modes of operation related the regulation technology used for a stimulation treatment:

Manual: in this mode, the regulation technology is selected by the NMES device's operator. The NMES device can recommend the best regulation technology based on the assessment of the resistance of the stimulated system but the operator can overlook that recommendation and select another regulation technology. This mode is intended for experienced operators that are familiar with electrical stimulation and understand the difference between current and voltage regulation.

Automatic: in this mode, the NMES device will select the most efficient regulation technology based on the assessment of the resistance of the stimulated system. The NMES device's operator will be informed of the selected technology but will not have the possibility to change it.

Hardware Implementation

In order to implement the present invention, the NMES device must provide the following features:

Measure of the electrical charge

Electronic circuit supporting both voltage and current regulation

Measure of the Electrical Charge

Figure 12:
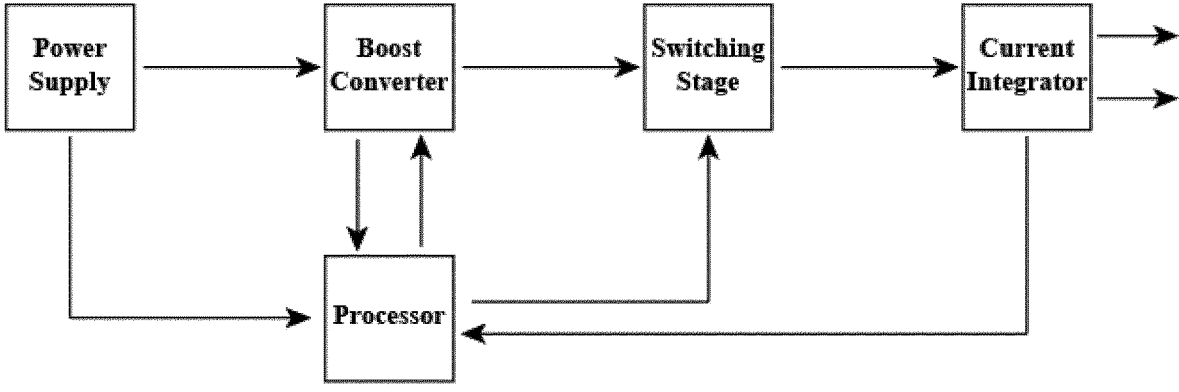
FIG. 12 shows a structural diagram of the NMES.

In order to assess the resistance of the stimulated system as described in the previous paragraph, the NMES device must be able to measure the electrical charge delivered to the stimulated system. This can be done by either integrating the electrical current delivered to the stimulated system with specific electronic components or by another method (i.e. as described on the previous patent: Electric Charge Control for TENS and NMES Devices). FIG. 12 shows a structural diagram of the NMES device where the Current Integrator block will provide feedback related to the electrical charge to the processor which will then select or recommend the most suitable regulation technology.

Electronic Circuit Supporting Both Voltage and Current Regulation

It is the object of the present invention to share most of the electronic components forming the switching stage between the two regulation technologies thus, reducing the number of components that would be required by having a distinct circuit for each regulation technology.

Figure 13:
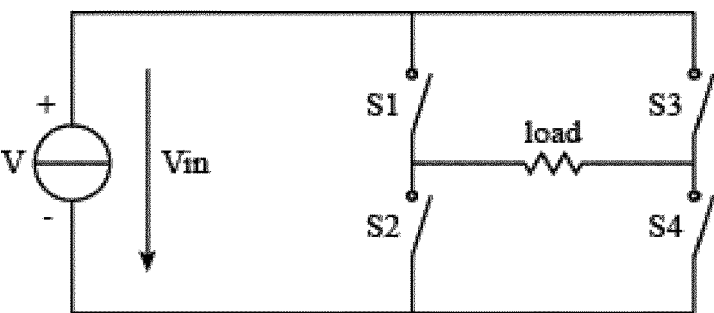
FIG. 13 shows the principle of a H-bridge circuit.

A typical topology for the switching stage of the present invention consists of a H-bridge circuit allowing for the delivery of electrical impulses of positive and negative polarity. FIG. 13 shows the principle of a h-bridge circuit.

H-Bridge Principle of Operation

H-bridges are available as integrated circuits, or can be built from discrete components.

Figure 14:
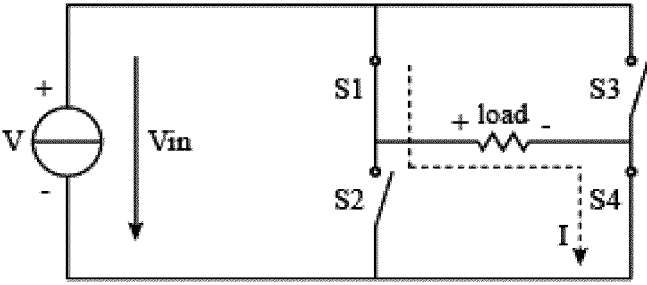
FIG. 14 shows the H-bridge in a first state.

The term H-bridge is derived from the typical graphical representation of such a circuit as shown in FIG. 13 An H-bridge is built with four switches (solid-state or mechanical). In the present invention these switches are implemented with bipolar junction transistors (BJT) or MOSFET transistors. As shown in FIG. 14, when the switches S1 and S4 are closed and S2 and S3 are open a voltage with given polarity is applied across the load and an electrical current I flow through the load (i.e. the H-bridge is in a first state).

Figure 15:
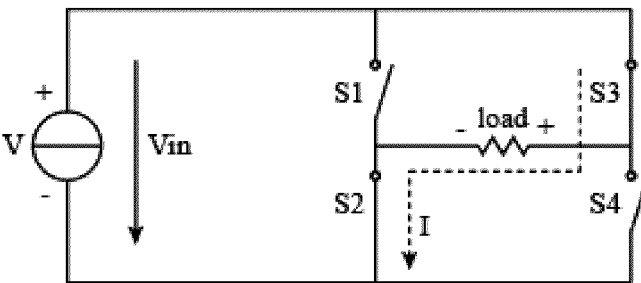
FIG. 15 shows the H-bridge in a second state.

By opening S1 and S4 switches and closing S2 and S3 switches, this voltage is reversed, reversing the voltage polarity on the load and the direction of the electrical current as shown in FIG. 15 (i.e. the H-bridge is in a second state).

Using the nomenclature above, the switches S1 and S2 should never be closed at the same time, as this would cause a short circuit on the input voltage source. The same applies to the switches S3 and S4. This condition is known as shoot-through.

Implementation of Both Regulation Technologies

FIG. 2 shows the embodiment of the switching stage (11) for the present invention. The components forming the h-bridge (13) are common to both technologies. The components driving the four switches are specific for current regulation (16) and for voltage regulation (15) technologies.

Current Regulation Operation

When the NMES device operates under current regulation the following parameters are applied:

The voltage provided by the Boost Converter stage (8) is set to the maximal value.

The Current Control Regulation (16) components will drive the switches of the h-bridge in order to regulate the electrical current flowing through the h-bridge and the stimulated system. The electrical current is set by the NMES device's operator. In this case the switches will operate as variable resistors to maintain a constant electrical current.

Voltage Regulation Operation

When the NMES device operates under voltage regulation the following parameters are applied:

The voltage provided by the Boost Converter stage (8) is set by the NMES device's operator.

The Voltage Control Regulation (15) components will drive the switches of the h-bridge in order the deliver the maximal electrical current. In this case the switches will act as simple switches with an internal resistance as low as possible.

Embodiments

1. A device for providing electrical stimulation to muscles and nerves featuring two distinct regulation technologies.

2. The device of embodiment 1 wherein the first regulation technology is voltage regulation.

3. The device of embodiment 1 wherein the second regulation technology is electrical current regulation.

4. The device of embodiment 1 wherein only one of the two regulation technologies can be enabled at a specific time.

5. A method for enabling the automated selection of the regulation technology.

6. The method of embodiment 5 wherein the most efficient regulation technology is assessed by the physiological response of the stimulated object (individual).

7. The method of embodiment 5 wherein the regulation technology can be switched from one technology to the other during the delivery of the stimulation.

8. A method for providing an electrical stimulation impulse to a user, comprising:

providing a conductive medium configured to apply the electrical stimulation impulse to a user;

providing a voltage regulator, configured to regulate the voltage applied during the electrical stimulation impulse;

providing a current regulator, configured to regulate the current applied during the electrical stimulation impulse; and determining, at a selector module, which of voltage regulation and current regulation will deliver more charge during the stimulation impulse; and outputting a result of the determination.

9. The method according to embodiment 8, further comprising:

selecting and activating either the voltage regulator or the current regulator, selecting whichever is determined will deliver more charge.

10. The method according to embodiment 8, further comprising:

displaying the result of the determination on a user interface; and receiving a selection of voltage or current regulation from a user via the user interface.

11. The method according to any one of embodiment 8 to 10, wherein the conductive medium comprises at least two terminals, and wherein, determining which of voltage and current regulation will deliver more charge during the electrical stimulation impulse comprises:

calculating a resistance between the terminals; and making the determination based on the calculated resistance.

12. The method according to embodiment 11, wherein calculating a resistance between the terminals comprises:

selecting voltage regulation;

delivering a test voltage through the terminals of the conductive medium for a time period;

measuring the electrical charge delivered through the terminals of the conductive medium during the time period; and calculating the resistance between the terminals based at least on the measured electrical charge and the time period.

13. The method according to embodiment 11 or 12, further comprising:

calculating a resistance value, $R_{mid}$, for which voltage regulation and current regulation would deliver equal charge;

comparing $R_{mid}$ to the resistance calculated between the terminals; and determining that voltage regulation will deliver more charge during the electrical stimulation impulse if the resistance calculated between the terminals is lower than $R_{mid}$, and determining that current regulation will deliver more charge during the electrical stimulation impulse if the resistance calculated between the terminals is greater than $R_{mid}$.

14. The method according to any one of embodiments 8 to 13, further comprising:

after activating either the voltage regulator or the current regulator, delivering the electrical stimulation impulse;

repeating the determination, output, selection, and activation of either the voltage regulation or the current regulation; and delivering a further electrical stimulation impulse.

15. A data processing apparatus comprising means for carrying out the steps of any one of embodiments 8 to 14.

16. A computer program, comprising instructions which, when the program is executed by a computer, cause the computer program to carry out the steps of any one of embodiments 8 to 14.

17. A computer readable storage medium having stored thereon the computer program of embodiment 16.

18. A device for providing electrical stimulation impulses to a user, comprising a data processing apparatus according to embodiment 15 or a computer readable storage medium according to embodiment 17.

The invention claimed is:

1. A device for providing an electrical stimulation impulse to a user, comprising:

a conductive medium configured to apply the electrical stimulation impulse to a user;

a voltage regulator, configured to regulate the voltage applied during the electrical stimulation impulse;

a current regulator, configured to regulate the current applied during the electrical stimulation impulse; and a selector module, configured to:

determine which of voltage regulation and current regulation will deliver more charge during the electrical stimulation impulse; and output a result of the determination;

wherein the selector module is further configured to:

select and activate either the voltage regulator or the current regulator, selecting and activating whichever is determined will deliver more charge during the electrical stimulation impulse.

2. The device according to claim 1, wherein the device further comprises:

a display, configured to display the result of the determination; and a user interface, configured to receive a selection of voltage or current regulation from a user, and wherein the selector module is further configured to:

activate either the voltage regulator or the current regulator, activating whichever is selected by the user via the user interface.

3. The device according to claim 1, wherein the conductive medium comprises at least two terminals, and wherein, when determining which of voltage and current regulation will deliver more charge during the electrical stimulation impulse, the selector module is further configured to:

calculate a resistance between the terminals; and make the determination based on the calculated resistance.

4. The device according to claim 3, wherein, when calculating a resistance between the terminals, the selector module is further configured to:

select voltage regulation;

deliver a test voltage through the terminals of the conductive medium for a time period;

measure the electrical charge delivered through the terminals of the conductive medium during the time period; and calculate the resistance between the terminals based at least on the measured electrical charge and the time period.

5. The device according to claim 4, wherein the test voltage is selected by the selection module to be sufficiently low so as not to be perceived by a user when delivered through the terminals of the conductive medium.

6. The device according to claim 3, wherein the selector module is further configured to:

calculate a resistance value, $R_{mid}$, for which voltage regulation and current regulation would deliver equal charge;

compare $R_{mid}$ to the resistance calculated between the terminals; and determine that voltage regulation will deliver more charge during the electrical stimulation impulse if the resistance calculated between the terminals is lower than $R_{mid}$, and determine that current regulation will deliver more charge during the electrical stimulation impulse if the resistance calculated between the terminals is greater than $R_{mid}$.

7. The device according to claim 3, further comprising a current integrator configured to measure the electrical charge delivered through the terminals of the conductive medium during the time period.

8. The device according to claim 1, wherein the voltage regulator and the current regulator share at least one electrical component with one another.

9. The device according to claim 8, wherein the at least one shared electrical component comprises an H-bridge and/or a boost converter.

10. The device according to claim 8, wherein when the voltage regulator is active:

the boost converter provides a voltage set by the device;

the voltage regulator drives switches of the H-bridge to deliver maximum electric current.

11. The device according to claim 8, wherein when the current regulator is active:

the boost converter provides a maximum voltage;

the current regulator drives switches of the H-bridge to maintain a constant electrical current.

12. The device according to claim 1, wherein the selection module comprises a plurality of switches configured selectively to connect the voltage regulator and the current regulator to the conductive medium.

13. The device according to claim 1, wherein, after activating either the voltage regulator or the current regulator, the device is configured to:

deliver the electrical stimulation impulse.

14. The device according to claim 13, wherein, after delivering the electrical stimulation impulse, the device is further configured to:

repeat the determination, output, selection, and activation of either voltage regulation or current regulation.

15. A method for providing an electrical stimulation impulse to a user, comprising:

providing a conductive medium configured to apply the electrical stimulation impulse to a user;

providing a voltage regulator, configured to regulate the voltage applied during the electrical stimulation impulse;

providing a current regulator, configured to regulate the current applied during the electrical stimulation impulse; and determining, at a selector module, which of voltage regulation and current regulation will deliver more charge during the stimulation impulse;

outputting a result of the determination; and selecting and activating either the voltage regulator or the current regulator, selecting whichever is determined will deliver more charge.

16. The method according to claim 15, further comprising:

displaying the result of the determination on a user interface; and receiving a selection of voltage or current regulation from a user via the user interface.

17. The method according to claim 15, wherein the conductive medium comprises at least two terminals, and wherein, determining which of voltage and current regulation will deliver more charge during the electrical stimulation impulse comprises:

calculating a resistance between the terminals; and making the determination based on the calculated resistance.

18. The method according to claim 17, wherein calculating a resistance between the terminals comprises:

selecting voltage regulation;

delivering a test voltage through the terminals of the conductive medium for a time period;

measuring the electrical charge delivered through the terminals of the conductive medium during the time period; and calculating the resistance between the terminals based at least on the measured electrical charge and the time period.

19. The method according to claim 17, further comprising:

calculating a resistance value, $R_{mid}$, for which voltage regulation and current regulation would deliver equal charge;

comparing $R_{mid}$ to the resistance calculated between the terminals; and determining that voltage regulation will deliver more charge during the electrical stimulation impulse if the resistance calculated between the terminals is lower than $R_{mid}$, and determining that current regulation will deliver more charge during the electrical stimulation impulse if the resistance calculated between the terminals is greater than $R_{mid}$.

20. The method according to claim 15, further comprising:

after activating either the voltage regulator or the current regulator, delivering the electrical stimulation impulse;

repeating the determination, output, selection, and activation of either the voltage regulation or the current regulation; and delivering a further electrical stimulation impulse.

* * * * *